(12) United States Patent
Cizek

(10) Patent No.: US 8,798,346 B2
(45) Date of Patent: Aug. 5, 2014

(54) IMAGE REGISTRATION

(75) Inventor: Jiri Cizek, Köln (DE)

(73) Assignee: Sicat GmbH & Co. KG, Bonn (DE)

( * ) Notice: Subject to any disclaimer, the term of this patent is extended or adjusted under 35 U.S.C. 154(b) by 1235 days.

(21) Appl. No.: 12/522,575

(22) PCT Filed: Nov. 19, 2007

(86) PCT No.: PCT/EP2007/062510
§ 371 (c)(1),
(2), (4) Date: Dec. 29, 2009

(87) PCT Pub. No.: WO2008/083874
PCT Pub. Date: Jul. 17, 2008

(65) Prior Publication Data
US 2010/0124367 A1 May 20, 2010

(30) Foreign Application Priority Data
Jan. 11, 2007 (DE) .......................... 10 2007 001 684

(51) Int. Cl.
*G06K 9/00* (2006.01)
*G06T 7/00* (2006.01)
*A61C 7/00* (2006.01)

(52) U.S. Cl.
CPC ..... *G06T 7/0028* (2013.01); *G06T 2207/30004* (2013.01); *A61C 7/002* (2013.01)
USPC ............................................. 382/130; 378/62

(58) Field of Classification Search
USPC ............... 382/128, 130, 131, 132; 378/98.11, 378/98.12, 62, 38
See application file for complete search history.

(56) References Cited

U.S. PATENT DOCUMENTS

| 5,568,384 A | 10/1996 | Robb et al. |
| 5,842,858 A | 12/1998 | Truppe et al. |

(Continued)

FOREIGN PATENT DOCUMENTS

| DE | 199 63 440 | 7/2001 |
| DE | 100 49 942 | 4/2002 |

(Continued)

OTHER PUBLICATIONS

Ayoub, A. F. et al., "Towards building a photo-realistic virtual human face for craniomaxillofacial diagnosis and treatment planning," Int. J. Oral Maxillofac. Surg., 2007, vol. 36, pp. 423-428.

(Continued)

*Primary Examiner* — Hoon Song
(74) *Attorney, Agent, or Firm* — Millen, White, Zelano, Branigan, P.C.

(57) ABSTRACT

Disclosed is a method for defining a common reference system in a record of volume data that represents an area of a patient's jaw and is captured by means of an X-ray imaging process and a record of surface data, at least some of which represents the same area of the patient's jaw and which is captured by means of a process for measuring visible surfaces. Volume data and surface data are unhidden on a screen. An object, especially a tooth, which is recognizable in both the volume data and the surface data, is superimposed on each other as congruently as possible in a preliminary positioning step. A volume structure characterizing the object is extracted from the volume data, particularly as a type of edge image, and is made to overlap as much as possible with a corresponding surface structure of the surface data by means of a transformation function, the overlap of the volume structure being adjusted to the surface structure in iterative steps by optimizing a predefined quality level.

15 Claims, 4 Drawing Sheets

(56) References Cited

U.S. PATENT DOCUMENTS

Figure 1:

| | | | |
|---|---|---|---|
| 6,362,821 B1 | 3/2002 | Gibson et al. | |
| 6,563,941 B1 | 5/2003 | O'Donnell et al. | |
| 6,628,977 B2 | 9/2003 | Graumann et al. | |
| 6,845,175 B2 | 1/2005 | Kopelman et al. | |
| 6,856,310 B2 | 2/2005 | Ditt et al. | |
| 7,234,937 B2 | 6/2007 | Sachdeva et al. | |
| 7,367,801 B2 | 5/2008 | Saliger | |
| 7,397,934 B2 | 7/2008 | Bloch et al. | |
| 7,840,042 B2 * | 11/2010 | Kriveshko et al. | 382/128 |
| 8,113,829 B2 | 2/2012 | Sachdeva et al. | |
| 2001/0029334 A1 | 10/2001 | Graumann et al. | |
| 2003/0083759 A1 | 5/2003 | Ditt et al. | |
| 2003/0169913 A1 | 9/2003 | Kopelman et al. | |
| 2003/0216631 A1 | 11/2003 | Bloch et al. | |
| 2004/0015327 A1 | 1/2004 | Sachdeva et al. | |
| 2005/0031176 A1 | 2/2005 | Hertel et al. | |
| 2006/0057534 A1 | 3/2006 | Saliger | |
| 2007/0012101 A1 | 1/2007 | Rottger et al. | |
| 2007/0207437 A1 | 9/2007 | Sachdeva et al. | |
| 2008/0064949 A1 | 3/2008 | Hertel et al. | |

FOREIGN PATENT DOCUMENTS

| | | |
|---|---|---|
| DE | 101 49 795 | 4/2003 |
| DE | 102 50 006 | 5/2004 |
| DE | 10 2005 024 949 | 12/2006 |
| EP | 10 18 709 | 7/2000 |
| JP | 08 131403 | 5/1996 |
| JP | 2002 528215 | 9/2002 |
| JP | 2003 517361 | 5/2003 |
| JP | 2003 532125 | 10/2003 |
| JP | 2005 521502 | 7/2005 |
| JP | 2006 204330 | 8/2006 |
| WO | WO-01 80761 | 11/2001 |

OTHER PUBLICATIONS

Cizek, J. et al., "Brain Studies—image co-registration and template creation," Nuc. Med. Rev., 2001, vol. 4, No. 1, pp. 43-45.

English Translation of Office Action for Related Japanese Patent Application No. 2009 545120 dated Oct. 23, 2012.

Hitachi Medical Corp., "Image Display Device," Patent Abstracts of Japan, Publication Date Aug. 10, 2006; English Abstract of JP-2006 204330.

International Search Report for PCT/EP2077/062510, Date of Completion: Mar. 6, 2008, Date of Mailing: Jul. 1, 2008.

Khambay, B. et al., "3D sterophotogrammetic image superimposition onto 3D CT scan Images: the future of orthognathic surgery. A Pilot study," International Journal Adult Orthodon Orthognath Surg., 2002, vol. 17, No. 4, pp. 331-341.

Method and system for scanning a surface and generating a three-dimensional object, Espacenet, Publication Date: Oct. 28, 2003; English Abstract of JP-2003 532125.

Nkienke, E. et al., "Fusion of computed tomography data optical 3D images of the dentition for streak artifact correction in the simulation of orthognathic surgery," Dentomaxiollofacial Radiology, 2004, vol. 33, pp. 226-232.

Uechi, J. et al., "A novel method for the 3-dimensional simulation of orthognathic surgery by using a multimodal image-fusion technique," Am. J. Orthod Dentofacial Orthop, 2006, vol. 130, pp. 786-798.

Wolf Henning, "Volume and surface measurement method used in forensic medicine for corpses involves determining volume data set and surface data set independently from same body and determining additional surface from volume data set," Espacenet, Publication Date: Apr. 18, 2002; DE-100 499 42.

Toshiba Medical Eng Co Ltd., "Medical Image Processor," Thomson Innovation, Publication Date: May 28, 1996; English Abstract of JP-08 131403.

* cited by examiner

IMAGE REGISTRATION

This invention relates to a process for defining a common reference system in a set of volume data that represents an area of a patient's jaw and that is recorded by means of an x-ray imaging process, and a set of surface data, at least some of which represents the same area of the patient's jaw and which is recorded by means of a process for recording visible surfaces.

Such a "registration" of two sets of data is always necessary if the latter were generated with various systems and/or at various times and are produced from the transfer of the sets of data for the processing of relevant information. Thus, for example, for planning an operation, for example an implantation, computer tomographic (CT) or cone beam x-ray images of a patient's jaw are taken, which contain detailed anatomical information. In contrast, for planning and producing dental prosthetic supplies, 3D surface images are taken directly from the jaw, or from a mold of the jaw, with an optical recording unit, for example a CEREC measuring camera from the Sirona Dental Systems Company GmbH. In contrast to the tomographical images, these surface data contain specific information on the course of the visible surface of the jaw, in particular the surface of the teeth and the mucous membrane. The visible surface is thus picked up accurately by this process.

The combination (fusion) of these two sets of data generates valuable additional information, which can be used both in the planning and implementation of the operation and in the planning and production of prosthetic supplies. Up until now, only processes for registering those sets of data that operate using models, markers or similar mechanical aids have been known.

From one publication (Nkenke, E., Zachow, S. et al.: *Fusion of Computer Tomography Data and Optical 3D Images of the Dentition for Streak Artifact Correction in the Simulation of Orthognathic Surgery*. Dentomaxillofacial Radiology (2004), 33, 226-232), a prototype of the registration of an x-ray data set of the jaw and the surface data set of a corresponding plaster model is known. In this case, first the visible surface, i.e., the surface of the teeth and the mucous membrane, is extracted from the x-ray image of the plaster model before said visible surface is then registered with the surface from the optical image using an ICP algorithm ("iterative closest point"). In practice, however, this process is hardly usable, since the extraction of the surface from the x-ray data set of a real patient is inaccurate, such that the requirements for a specific registration of the surfaces are not met.

Moreover, the use of reference elements (markers) is known. Because of the associated problems of attachment and the difficulties for patients, however, markers are only used when there is no simpler option. Thus, for example, U.S. Pat. No. 5,842,858 discloses a process in which during the x-ray imaging, the patient carries a template with markers; the template is then placed on the model to which a sensor is attached for 3D-position detection. After the positional relationship between the sensor and the markers is determined, the template can be removed, and optical imaging can be done. In this case, the 3D sensor makes possible the registration relative to the patient imaging.

The object of the invention is now to provide a process for registering a volume-data set of a real patient and a set of corresponding surface data, which can be converted directly by the attending physician simply and conveniently without additional aids.

This object is achieved by the process according to claim 1. Advantageous embodiments are mentioned in the subclaims.

The essential idea of the invention can be paraphrased as follows: Starting from the tomographically recorded volume data and the surface data, the two sets of data are advantageously depicted together in one image or optionally also in two separate images on a screen, whereby the mutual orientation of the objects visible therein is initially still relatively insignificant. The objects are ideally teeth, which are readily detectable in both visualizations. On the screen, in a kind of prepositioning, a visualization of a marking object is "manually" placed over the other visualization of the object as well as possible, for example by guiding with a cursor. Then, by means of a transformation function, a marking volume structure that is extracted from the volume data, which is formed by, for example, edges of the object, with the corresponding structure of the surface data, named surface structure below, is positioned overtop as much as possible, whereby a measure of the quality of the uniformity of intersection is defined and whereby the extracted structure in iterative steps under optimization of the quality criterion is matched to the surface structure that can be seen in the surface data.

The idea that is essential to the invention is thus to contain the complete relevant information from the x-ray volume data set and to convert it into another volume form, namely that of the marking volume structure. This then makes possible the direct comparison with the corresponding location on the surface of the optical image. In a way according to the invention, the coordinates of the optical image are automatically positioned overtop by iteration with the coordinates of the x-ray image. The invention thus represents a process that makes possible a precise and automated registration of an optical image with an x-ray image of a patient. With this process, the registration, in which the optical image is overlapped in space with the tomographical image, can be performed without using any external reference elements, physical models, such as plaster models, or mechanical devices. This registration is automated to a large extent and can be performed in an amount of time on the order of magnitude of, for example, 15-30 seconds.

The fusion of the two data sets performed in such a way is helpful both for the planning and for the implementation of operation and can also be used in prosthetic supplies. Thus, for example, in implantation planning, in addition to the anatomical information from the x-ray data set, the exact course of the surface of the mucous membrane can also be examined, which, as already stated, cannot be detected to the desired extent in the volume data recorded by x-ray. Another application is also to integrate the prosthetic information when using the CEREC system and to implement a kind of implantation planning that is based on both anatomy and prosthetics. In addition, artifacts in x-ray data sets can be reduced, which are caused by, for example, metal fillings. By the fusion of the data set with an optical image of the jaw, which is completely free of any metal artifacts, the outer contours of the patient's data set can be correctly reproduced with simultaneous visualization of the relevant volume information.

For a largely automatic prepositioning, it is especially advantageous if the user defines reference points on the object or objects in the first visualization of the two data sets. The latter can then be superimposed by the graphics program, so that already a first approximation to an overlap of the data sets is given. The accuracy at this stage does not need to be especially exact, but rather it has to lie within a specific tolerance. For this automatic prepositioning, at least a first reference point is defined on the surface of the object that is depicted in the volume data, in particular on the surface of a tooth, and at least a second reference point is defined on at least almost the same location on the surface thereof also in the object that is visible in the surface data, especially the same tooth. As pointed out, in the automatic prepositioning, the reference points that correspond to the object are placed on top of one another as much as possible by means of an automatically calculated transformation. Depending on the number of reference points, this transformation advantageously corresponds to an analytically determined shift (a reference point) or shift with rotation (two reference points) or a shift with rotation (three and more reference points) determined by means of a least-square-minimization process (also known as "point-based registration"). Advantageously, the reference points of the user being considered are defined on the screen by means of a cursor that can be moved over the screen, in particular by means of mouse clicks.

The user can be supported by the software when setting the reference points. Thus, for example, suitable reference points in the surface data can automatically be proposed by the software, whereby it is then the object of the user to mark the corresponding reference points in the volume data set.

Figure 2:
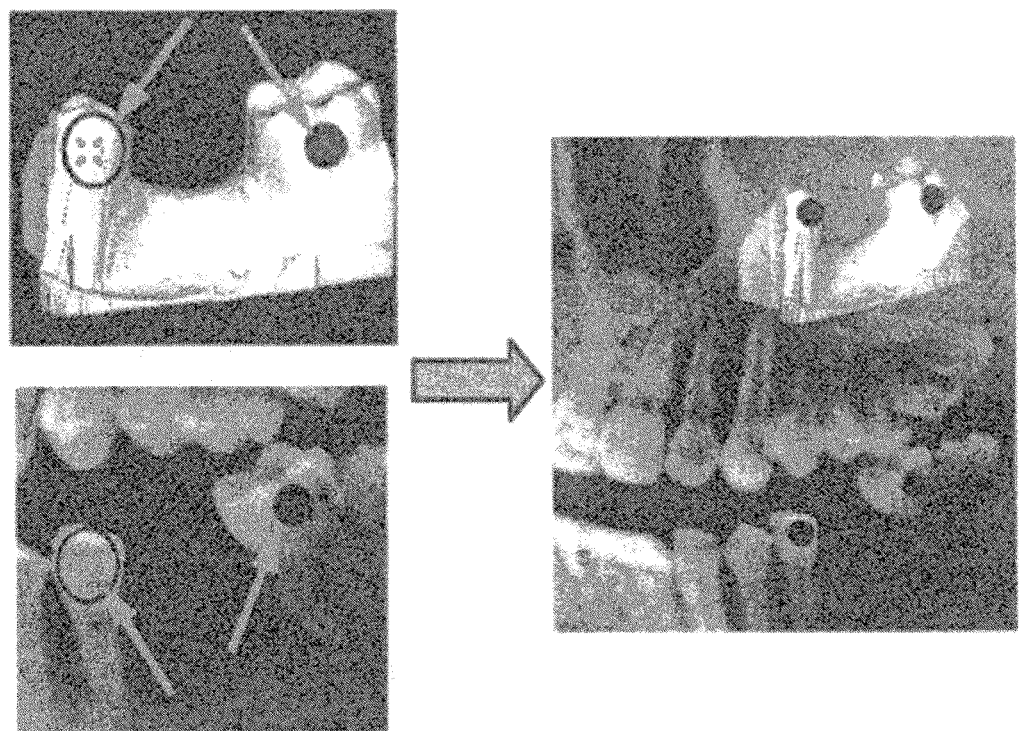
Figure 3:
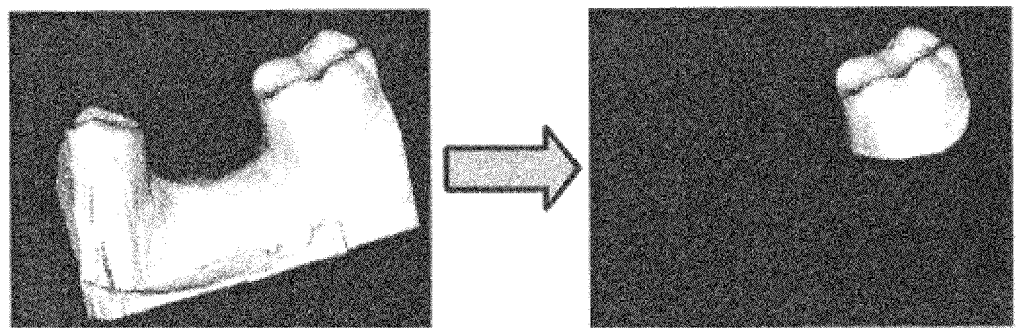
Figure 4:
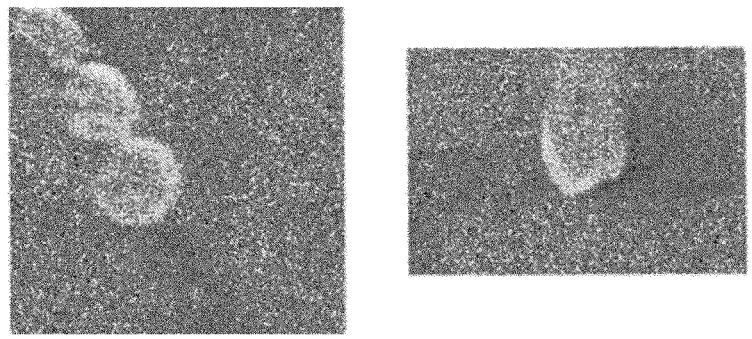
Figure 5:
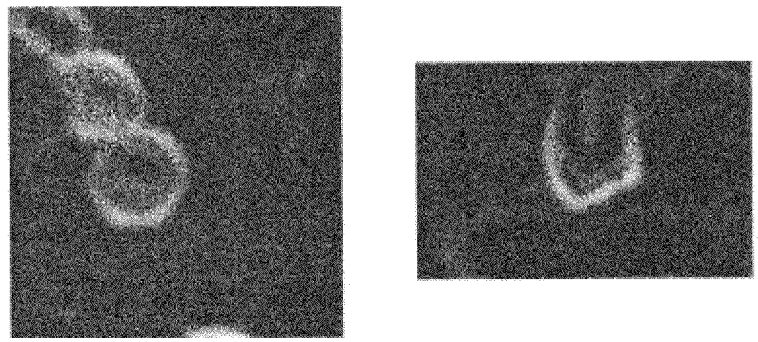
Figure 6:
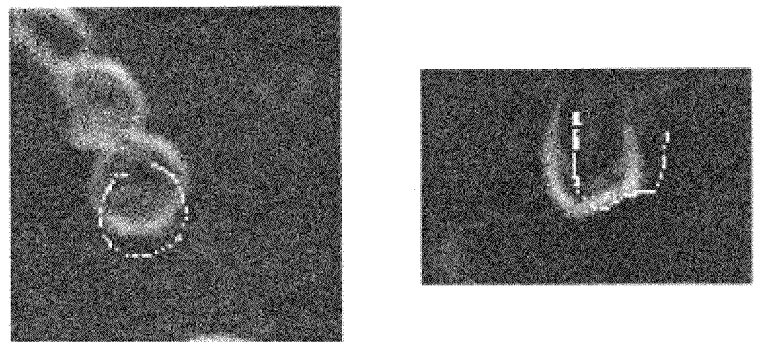
Figure 7:
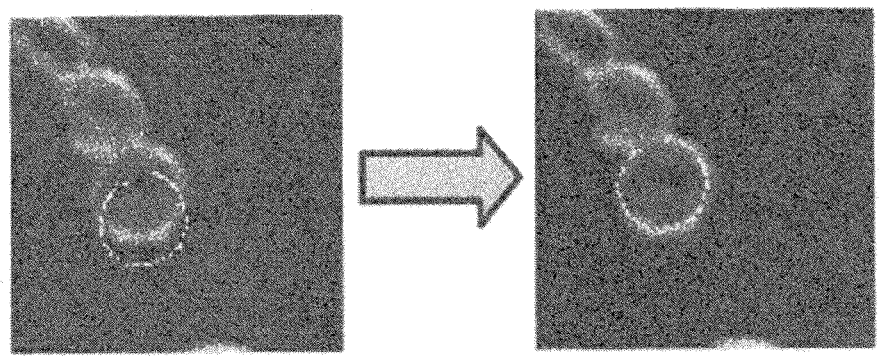
Figure 8:
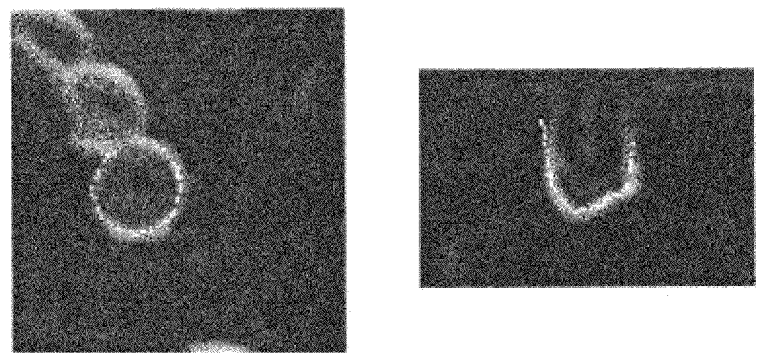
Figure 9:
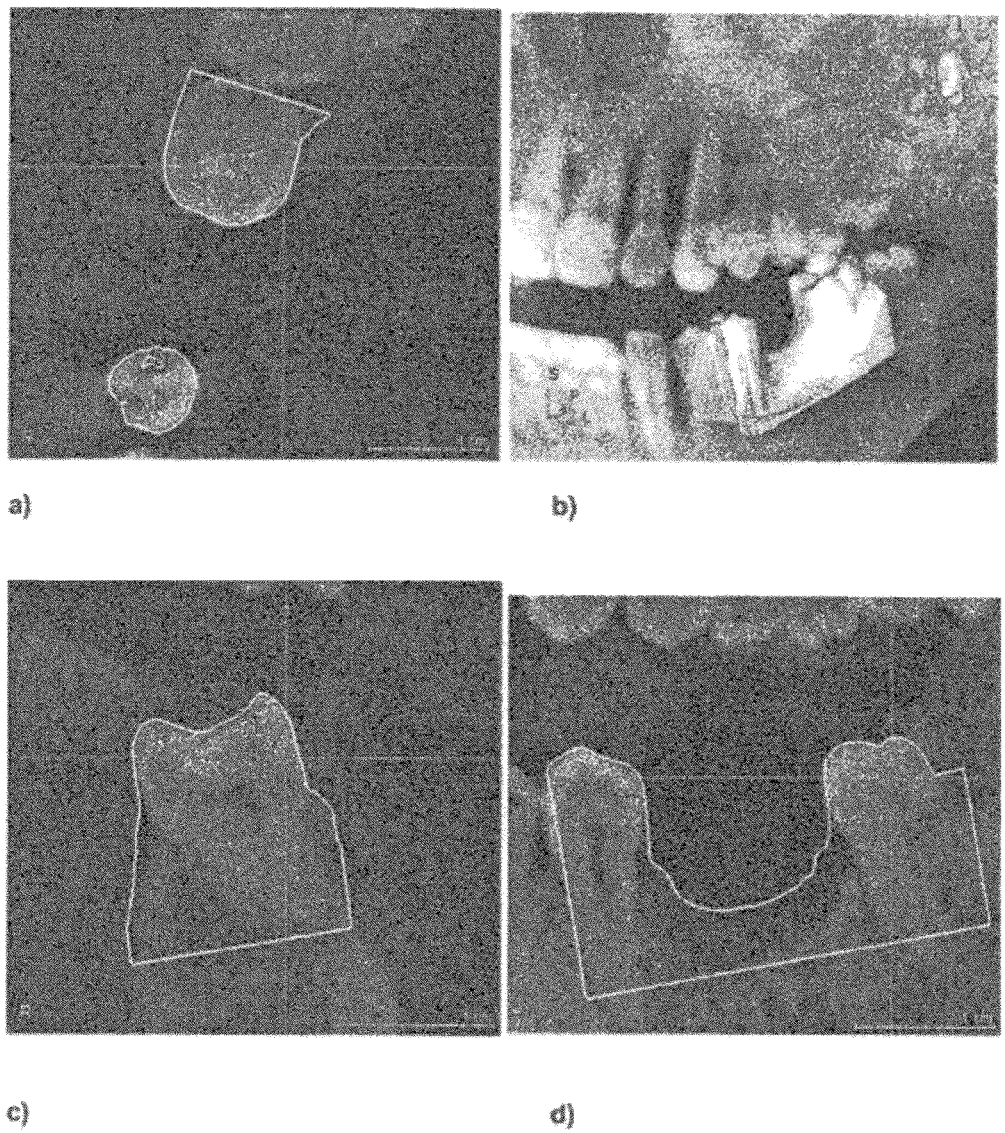

Below, the procedure according to the invention is explained in more detail based on FIGS. 1 to 9. In this case:

FIG. 1 shows the initial position of the optical surface image and the x-ray image in space, FIG. 2 shows the marking of the positions of the adjacent teeth on the surface of the optical image and in the volume of the x-ray image, FIG. 3 shows the extraction of the 3D test points from the optical surface image, FIG. 4 shows the extraction of the 3D test volume from the tomographic image, FIG. 5 shows the generation of an optionally smoothed 3D edge image from the 3D test volume, FIG. 6 shows the superimposing of the extracted test points in the test volume, FIG. 7 shows the automatic search for a suitable transformation (shift in 3D+rotation in 3D), which positions overtop the extracted points with the edges in the test volumes, FIG. 8 shows the result of the automatic optimization, and FIG. 9 shows the superimposing of the calculated transformation on the complete optical image.

FIG. 1 shows the initial situation. Tomographically recorded volume data of the jaw area of a patient are shown on a screen. Surface data of a partial area that are recorded with an optical process are integrated into this visualization, whereby these surface data are clearly in the "wrong" place since they show two tooth fragments from the lower jaw. The data are read by means of a program that also makes it possible to examine two data sets in a 3D view in their original position interactively from various points of view.

In FIG. 2, the next step is shown: the user marks the respective visualization of the same tooth in each case in both data sets. In this case, the marking is carried out by one mouse click in the 3D view and is visualized by one point. The labeled points (arrows) form reference points, which are used in a great prepositioning of the data sets and in this case help the amount of information, which is present in the data sets, to reduce the essential. Using the reference points, an initial transformation is performed as prepositioning, in which the two data sets are roughly positioned overtop. This prepositioning is not especially exact. It lies in a "capture range" of the subsequent automatic optimization, however.

In FIG. 3, the extraction of the 3D test points from the surface data is shown. To this end, all points are extracted from the surface data for each reference point, and the removal of said points is smaller at the respective reference point than a preset threshold value, which is approximately one cm here. These points form the "test points," which in this case describe one complete molar of the two marked lower molars. The totality of the test points forms the surface structure that later serves for comparison with the volume structure.

A similar procedure is employed in the next step, shown in FIG. 4, in which for each reference point, a 3D test volume is first extracted from the tomographic image. To this end, around each of the reference points that are set in the volume data, a small parallelepiped area, the test volume, is extracted, which is shown here axially a) and sagitally b). This test volume is converted by a convolution with several suitable convolution filters into 3D edge images, whereby in these edge visualizations, the edges of the teeth in question can be clearly detected (FIG. 5). These edge visualizations form the geometric volume structure that characterizes the object, which is compared to the surface structure.

Since the noise in the original image influences such an edge detection, a 3D smoothing can then be performed with a suitable smoothing filter, such as a Gauss filter or a median filter. As a result, the capture range of the optimization algorithm is enlarged. The brightest areas in the following figure correspond to the most prominent edges in the test volume.

In the next step according to FIG. 6, the extracted test points in the test volume are superimposed before a transformation is attempted, which transforms the test points so that they coincide with the edges in the edge images (FIG. 7). The automatic search for a suitable transformation takes place by a three-dimensional shift and a three-dimensional rotation, which positions the extracted points overtop with the edges in the test volume.

Then, a cost function is defined that indicates how well the test points from the surface data agree with the corresponding edge image. The cost function is a function of the six parameters of a rigid element transformation, whereby three parameters for the shift and three parameters for the rotation are required. In this case, the cost function is defined and calculated as follows for a specific transformation T: First, all extracted points with the transformation T are transformed into the corresponding extracted volume. For each point from the optical image, the corresponding value ("brightness") is determined in the edge image by interpolation. The sum of the values of all test points, averaged by the number of points, gives the overall value of the cost function for the transformation T.

The cost function can also have other forms that improve the robustness, speed or precision of the optimization or make the optimization insensitive to outliers in the data. Thus, for example, only a portion of the points, which have the highest brightness values, can be included in the calculation.

In the next step, the transformation is sought for which the cost function takes its maximum value. The search is carried out using an iterative optimization algorithm. FIG. 8 shows the result of the automatic optimization.

FIG. 9 shows the transfer of the calculated transformation onto the complete optical image and thus the result of the image registration of a real set of patient data: as the contours indicated with the white line show according to a), c) and d), the surface data set with the teeth was positioned overtop. It can also be seen that the course of the visible surface, which is formed by the mucous membrane, represents additional information. Especially in FIG. 9 c), it is clear that the white line "fits" extremely well in the area of the tooth, whereby the mucous membrane detaches at the neck of the tooth.

In this case, the automatic steps last no longer than a few seconds with use of a commercially available PC.

The invention claimed is:

1. Process for defining a common reference system in a set of volume data that represents an area of a patient's jaw and that is recorded with an x-ray imaging process, and a set of surface data, at least some of which represents the same area of the patient's jaw and which is recorded with a process for measuring visible surfaces, comprising:
    integrating the volume data and surface data on a screen,
    in a prepositioning, superimposing an object detected both in the volume data and in the surface data, as precisely as possible,
    extracting a volume structure that characterizes the object, in particular in the form of an edge image, from the volume data, and said edge image is superimposed as much as possible by means of a transformation function with a corresponding surface structure of the surface data, and
    matching the overlap of the volume structure under optimization of a specified quality criterion in iterative steps to the surface structure.

2. Process for defining a common reference system in a set of volume data that represents an area of a patient's jaw and that is recorded with an x-ray imaging process, and a set of surface data, at least some of which represents the same area of the patient's jaw and which is recorded with a process for measuring visible surfaces,
wherein
    the volume data and surface data are integrated on a screen,
    in a prepositioning, an object, especially a tooth, which can be detected both in the volume data and in the surface data, is superimposed as precisely as possible,
    a volume structure that characterizes the object, in particular in the form of an edge image, is extracted from the volume data, and said edge image is superimposed as much as possible by means of a transformation function with a corresponding surface structure of the surface data, and
    the overlap of the volume structure under optimization of a specified quality criterion is matched in iterative steps to the surface structure, and
    wherein for the prepositioning, at least a first reference point is defined on the surface of the object that is depicted in the 3D volume data, in particular on a tooth, and at least a second reference point is defined on at least almost the same place on the surface of the object that is also visible in the 3D surface data, whereby in the prepositioning, the corresponding reference points of the volume data and the surface data are placed on top of one another as much as possible by means of an automatically calculated transformation.

3. Process according to claim 2, wherein the reference points in the surface data are proposed automatically by the software, and the corresponding reference points are marked in the volume data by the user.

4. Process according to claim 2, wherein the reference points are defined by the observer on the screen by means of a cursor that can move over the screen, in particular by means of mouse clicks.

5. Process for defining a common reference system in a set of volume data that represents an area of a patient's jaw and that is recorded with an x-ray imaging process, and a set of surface data, at least some of which represents the same area of the patient's jaw and which is recorded with a process for measuring visible surfaces, wherein
    the volume data and surface data are integrated on a screen,
    in a prepositioning, an object, especially a tooth, which can be detected both in the volume data and in the surface data, is superimposed as precisely as possible,
    a volume structure that characterizes the object, in particular in the form of an edge image, is extracted from the volume data, and said edge image is superimposed as much as possible by means of a transformation function with a corresponding surface structure of the surface data, and
    the overlap of the volume structure under optimization of a specified quality criterion is matched in iterative steps to the surface structure, and
    wherein after the prepositioning, relative to at least one reference point of the surface data, test points are extracted, whose removal at the respective reference point is smaller than a specified threshold value, whereby the test points form the surface structure.

6. Process according to claim 1, wherein after the prepositioning, a test volume is extracted for at least one reference point of the volume data.

7. Process according to claim 6, wherein an extracted test volume is converted by a mathematical operation with suitable filters in a 3D edge image, which forms the volume structure.

8. Process according to claim 6, wherein the edge information is smudged to ensure a higher tolerance.

9. Process according to claim 1, further comprising a transformation that transforms a plurality of test points so that they coincide with the edge images, whereby a quality of the coincidence is determined by a cost function.

10. Process according to claim 9, wherein the transformation is performed several times in iterative steps with optimization of the cost function.

11. Process according to claim 1, wherein all test points in the extracted test volume are transformed, and for each point from the optical image, a corresponding value for brightness in the edge image is determined by interpolation.

12. Process according to claim 11, wherein a cost function for the transformation T is calculated from all test points or a portion of the test points.

13. Process according to claim 12, wherein the total value of the cost function for the transformation T is determined from the sum of values of a portion of the test points that have the highest brightness values, averaged by the number of points.

14. Process according to claim 11, wherein the total value of the cost function for the transformation T is determined from the sum of the values of all test points, averaged by the number of points.

15. Process according to claim 1, wherein the surface data are recorded directly on the patient.

* * * * *